United States Patent
Giles et al.

(10) Patent No.: US 8,377,478 B2
(45) Date of Patent: Feb. 19, 2013

(54) SOLID DETERGENT COMPOSITION

(75) Inventors: Matthew Robert Giles, Hoole (GB); Nicholas John Dixon, Upton (GB)

(73) Assignee: Innospec Limited (GB)

( * ) Notice: Subject to any disclaimer, the term of this patent is extended or adjusted under 35 U.S.C. 154(b) by 0 days.

(21) Appl. No.: 12/666,119

(22) PCT Filed: Jul. 22, 2008

(86) PCT No.: PCT/GB2008/050610
§ 371 (c)(1), (2), (4) Date: Jan. 19, 2010

(87) PCT Pub. No.: WO2009/013539
PCT Pub. Date: Jan. 29, 2009

(65) Prior Publication Data
US 2010/0191012 A1 Jul. 29, 2010

(30) Foreign Application Priority Data
Jul. 26, 2007 (GB) .................................. 0714575.8

(51) Int. Cl.
C11D 17/06 (2006.01)
C11D 3/30 (2006.01)
C07C 229/06 (2006.01)

(52) U.S. Cl. .......................... 424/489; 510/490; 562/565

(58) Field of Classification Search ........................ None
See application file for complete search history.

(56) References Cited

U.S. PATENT DOCUMENTS

| | | | |
|---|---|---|---|
| 4,704,233 A | 11/1987 | Hartman et al. | |
| 5,780,419 A * | 7/1998 | Doumen et al. | 510/452 |
| 2002/0119136 A1* | 8/2002 | Johansen | 424/94.4 |
| 2010/0183533 A1 | 7/2010 | Giles et al. | |

FOREIGN PATENT DOCUMENTS

| | | |
|---|---|---|
| EP | 0713910 A2 | 10/1995 |
| EP | 0771864 A | 5/1997 |
| GB | 2294694 A | 11/1994 |
| GB | 2283494 A | 5/1995 |
| WO | 94/03553 A1 | 2/1994 |
| WO | 9702010 A | 6/1996 |
| WO | 9730209 A | 8/1997 |
| WO | 99/24392 A1 | 5/1999 |

OTHER PUBLICATIONS

Tandy et al, Environmental Science and Technology Extraction of Heavy Metals from Soils Using Biodegradable Chelating Agents, 2004, 38, pp. 937-944.*
Kovaleva et al, Zhurnal Neorganiskoi Khimii, Magnesium and Calcium Ethylenediaminedisuccinates, 1991, 36(3), pp. 664-669, English translation.*
International Preliminary Report on Patentability and Written Opinion of the International Search Authority, dated Jan. 26, 2010 from parent application PCT/GB2008/050610, filed on Jul. 22, 2008, which claims priority to Great Britain Patent Application No. 0714575.8, filed on Jul. 26 2007.
Database CA [Online] Chemical Abstracts Service, Columbus, Ohio, US; retrieved from STN Database accession No. 1991:440744.
Kovaleva, I.B. et al. "Magnesium and calcium ethylenediaminedisuccinates." Zhurnal Neorganicheskoi Khimii 36(3), 664-9 Coden: ZNOKAQ; ISSN: 0044-457X, 1991.
U.K. Intellectual Property Office Search Report under Section 17 dated Nov. 28, 2007 for GB0714575.8.
International Search Report dated Oct. 14, 2008 for PCT/GB08/050610.
Witschel et al., "Purification and characterization of a lyase from the EDTA-degrading bacterial strain DSM 9103 that catalyzes the splitting of [S,S]-ethylenediaminedisuccinate, a structural isomer of EDTA," Biodegration 8(6): 419-428 (1998).

* cited by examiner

*Primary Examiner* — Paul A Zucker
(74) *Attorney, Agent, or Firm* — Burns & Levinson, LLP; Janine M. Susan

(57) ABSTRACT

A salt of ethylenediamine disuccinic acid comprising at least 0.7 mole equivalents of magnesium per mole of ethylenediamine disuccinic acid which salt is in the form of a water-soluble, non-hygroscopic solid is disclosed. Also described is a method of preparing such salts and uses thereof.

14 Claims, No Drawings

SOLID DETERGENT COMPOSITION

CROSS-REFERENCE TO RELATED APPLICATIONS

This application is a U.S. national stage application under 35 U.S.C. 371 of co-pending International Application No. PCT/GB08/50610 filed Jul. 22, 2008 and entitled "COMPOSITION", which in turn claims priority to Great Britain Patent No. 0714575.8 filed Jul. 26, 2007, both of which are incorporated by reference herein in their entirety for all purposes.

The present invention relates to salts of ethylenediamine disuccinic acid (or EDDS). It also relates to methods of preparing such salts, uses thereof and compositions containing said salts. In particular the present invention relates to magnesium-containing salts of EDDS.

Ethylenediamine disuccinic acid has the structure shown in figure 1:

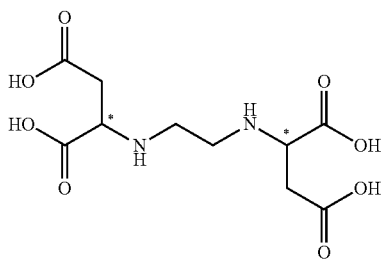

FIG. 1

The structure includes two stereogenic centres and three possible stereoisomers exist. An especially preferred configuration is S,S ethylenediamine disuccinic acid as this compound is readily biodegradable.

Compositions comprising ethylenediamine disuccinic acid and sodium salts thereof are very widely used particularly as chelating agents.

In this specification, the abbreviation "EDDS" is used to denote the structure show in figure 1 and said structure in which a number of the hydroxyl hydrogen atoms have been replaced i.e., "EDDS" may also be used to refer to succinate salts in which 1, 2, 3 or 4 of the acid groups have been neutralised or partially neutralised.

One commercially available material is trisodium ethylenediamine disuccinate. It can be purchased as an aqueous solution comprising 30 wt % EDDS (expressed as free acid) or 37 wt % of trisodium EDDS (including the counterion).

Ethylenediamine disuccinic acid is also commercially available in the form of a solid powder. This contains 65 wt % solid [S,S] EDDS as an acid, and water of crystallisation.

Because EDDS is an effective chelating agent, particularly of heavy metals and transition metals, it is often included in laundry and automatic dishwashing formulations.

Trisodium EDDS is readily water soluble and thus can be incorporated into dishwashing or laundry formulations. However many consumers prefer such products in the form of powders or compressed powder tablets and as such the provision of trisodium EDDS as a liquid composition causes considerable challenges for manufacturers during formulation. Whilst solid trisodium EDDS can be isolated as a white powder, it is very hygroscopic and rapidly absorbs water from the atmosphere.

The free tetra acid form is available in the form of a powder and so could be granulated. However it has a solubility of only 0.3 g/Kg in water which of course presents other problems with respect to its use in laundry and dishwashing applications.

There are many other situations where the lack of availability of a water soluble solid form of EDDS is a limitation to formulators of products.

The inventors have found a free flowing solid composition comprising EDDS which is readily water soluble, not hygroscopic under normal atmospheric conditions and can be easily granulated.

According to a first aspect of the present invention there is provided a salt of ethylenediamine disuccinic acid comprising at least 0.7 mole equivalents of magnesium per mole of ethylenediamine disuccinic acid which salt is in the form of a water-soluble, non-hygroscopic solid.

Preferably the salt is the form of a free flowing particulate material. It may be a powder or it may be granular.

Preferably the salt may be easily incorporated in a granular composition.

In some preferred embodiments the salt comprises at least 0.8 mole of magnesium per mole of ethylenediamine disuccinic acid, preferably at least 0.9 mole, more preferably at least 1 mole, preferably at least 1.3 moles, more preferably at least 1.5 moles, preferably at least 1.7 moles, more preferably at least 1.8 moles, preferably at least 1.9 moles, and most preferably approximately 2 moles.

In some embodiments, the salt may further comprise a second alkaline earth metal, for example, calcium. It may comprise up to 1.3 moles of calcium per mole of ethylenediamine disuccinic acid, for example up to 1.2 moles, for example up to 1.0 moles, up to 0.7 moles, or up to 0.5 moles.

Especially preferred salts include dimagnesium ethylenediamine disuccinic acid, i.e. the salt having 2 moles of magnesium per mole of ethylenediamine disuccinic acid. Thus a compound in which all 4 hydroxyl hydrogen atoms of figure 1 have been replaced by two magnesium ions is preferred.

Also highly preferred are salts having from 1 to 2 moles of magnesium per mole of ethylenediamine disuccinic acid. For example the compound having the formula magnesium EDDS (MgEDDS) is favoured as is calcium magnesium EDDS (CaMgEDDS). The salt having 1.5 molar equivalent of magnesium per mole of ethylenediamine disuccinic acid ($Mg_{1.5}$EDDS) has also been found to have advantageous properties.

In some embodiments the salt may include 0.05 or more moles of one or more alkali metals per mole of ethylenediamine disuccinic acid. Thus the salt may be a mixed salt containing one or more alkaline earth metals and one or more alkali metals. The alkali metal when present is preferably selected from sodium, potassium and mixtures thereof. Most preferably it is sodium. In some embodiments the salt comprises from 0.5 to 2 moles, preferably 1 to 2 moles, more preferably 1.5 to 2 moles of alkali metal per mole of ethylenediamine disuccinic acid. Thus the salt of the present invention may, for example, comprise a compound of empirical formula sodium magnesium EDDS, disodium magnesium EDDS, potassium magnesium EDDS, dipotassium magnesium EDDS, or non-stoichiometric equivalents thereof. The salt of empirical formula disodium magnesium EDDS has been found to have advantageous properties.

However in especially preferred embodiments, the salt of the present invention does not comprise an alkali metal. In especially preferred embodiments the salt comprises only alkaline earth metal and EDDS.

The "EDDS" portion of the salt of the present invention may include any of the stereoisomers. Thus it may be selected from [R,R]-EDDS, [R,S]-EDDS, [S,S]-EDDS and any combination thereof.

Preferably the salt comprises at least 50% [S,S]-EDDS, preferably at least 70%, more preferably at least 90%. In some preferred embodiments the salt consists essentially of a magnesium salt of [S,S]-EDDS.

The salt of the present invention is not hygroscopic under normal atmospheric conditions. Preferably the salt of the present invention absorbs less than 10% of its weight of water upon exposure to normal atmospheric conditions for 72 hours, preferably less than 5% of its weight, preferably less than 2.5%, more preferably less than 1.5% of its weight. Preferably it absorbs less than 5% of its weight of water upon exposure to normal atmospheric conditions for 96 hours, preferably less than 3% of its weight, preferably less than 1% of its weight, more preferably less than 0.5% preferably less than 0.1% and most preferably less than 0.05% of its weight. Preferably it absorbs less than 0.1% of its weight of water after exposure to normal atmospheric conditions for 14 days.

The salt of the present invention preferably has a solubility which provides a concentration of EDDS of at least 8 g/Kg, preferably at least 10 g/Kg in water at room temperature, preferably at least 50 g/Kg, more preferably at least 100 g/Kg, more preferably at least 125 g/Kg and most preferably at least 150 g/Kg. In some embodiments the salt may have a solubility of up to 200 g/Kg, preferably up to 190 g/Kg, more preferably up to 180 g/Kg and most preferably up to 175 g/Kg.

The above solubility values refer to the weight of succinate present in an aqueous solution, expressed as the weight of equivalent ethylene diamine disuccinic acid.

The solid form may include water of crystallisation. This may be present in an amount of from 5 to 45%, for example from 15 to 20%.

According to a second aspect of the present invention, there is provided a composition comprising a salt of the first aspect.

The composition may consist essentially of the salt of the first aspect or it may include one or more further components. The composition may be a solid composition or a liquid composition. The composition may be of the form of any composition in which trisodium EDDS or ethylenediamine disuccinic acid has previously been incorporated.

The composition may, for example, be a laundry composition or an automatic dishwashing composition. The composition may be in the form of a powder, for example a free flowing powder. Alternatively the composition may be in the form of compressed tablets, or encased, in liquid or solid form, in a shell of a water-soluble polymeric material.

The composition may be a granular composition.

Solid laundry compositions of the present invention preferably comprise from 0.01 to 10 wt %, more preferably 0.01 to 2 wt %, most preferably 0.1 to 0.5 wt % of a salt of the first aspect.

Liquid laundry compositions of the present invention preferably comprise from 0.01 to 25 wt %, more preferably 0.1 to 10 wt %, most preferably 1 to 5 wt % of a salt of the first aspect.

Automatic dishwashing compositions of the present invention preferably comprise 0.1 to 60 wt % of a salt of the first aspect, more preferably 1 to 30 wt % and most preferably 2 to 15 wt %.

Laundry and dishwashing compositions of the present invention preferably comprise further ingredients selected from surfactants, builders, bleaches, bleach activators, redeposition additives, dye transfer inhibitors, enzymes, colorants and fragrances.

The composition of the present invention may be a bleaching composition. It may be a cleaning composition. It may be personal care composition.

According to a third aspect of the present invention there is provided a method of preparing a salt according to the first aspect.

Preferably the method of the third aspect involves adding a base of magnesium to ethylenediamine disuccinic acid. Preferably the method comprises adding a magnesium base to a suspension of ethylenediamine disuccinic acid, preferably an aqueous suspension. Preferably this suspension comprises from 10 to 450, for example 50 to 200 grams of acid per litre of water.

Any suitable base can be used. For example, the base may be selected from carbonates, hydroxides, hydrides, amides and oxides. Preferably the base is magnesium hydroxide.

In some embodiments in which the salt comprises a mixed salt, the method of the third aspect may further comprise adding a calcium base and/or an alkali metal base to ethylenediamine disuccinic acid.

The present invention further provides the use of a salt of the first aspect in any manner in which EDDS-containing materials are used.

These compositions are particularly useful in paper and pulp bleaching. Compositions of this aspect may also find utility in laundry and dishwashing applications. As detailed above the salt of the first aspect may also be used in other bleaching applications.

The present invention thus provides the use of the salt of the first aspect as a chelating agent. In particular the salts of the first aspect of the present invention are used as chelating agents for binding transition metals and heavy metals, for example copper, iron and manganese.

Thus the present invention includes the use of a salt of the first aspect in detergent compositions, for example laundry or automatic dishwashing compositions.

The present invention includes the use of a salt of the first aspect in agricultural applications. For example the salt may be used in slug pellets, in herbicides, in foliar feeds, in nutrient feeds and in hydroponics.

The present invention provides the use of a salt of the first aspect in pulp and paper bleaching. This includes mechanical bleaching and chemical bleaching as well as thermo-mechanical bleaching. The salt of the first aspect may be used in the Q stage and the P stage of the pulp bleaching, that is the wash in which metals are removed and the peroxide stage in which bleaching occurs. These terms are well understood to those skilled in the art.

The present invention provides the use of a salt of the first aspect in personal care applications. For example the salt may be incorporated in hair care compositions, for example hair dyes and shampoo. It may also be included as an antioxidant in creams, for example sun creams and the like.

The present invention includes the use of a salt of the first aspect as a biocide potentiator. As such it may be able to increase the effectiveness of a biocide and may find wide application. For example it may be used in personal care applications.

The present invention provides the use of a salt of the first aspect in household, institutional and industrial cleaning applications. It may be included in hard surface cleaners, bathroom and kitchen cleaners, in bottle washing applications or in the cleaning of dairy equipment.

The present invention further provides the use of a salt of the first aspect as an anti-scalant material, for example as a sequestrant of calcium and magnesium salts.

The salt of the present invention may be used in oil field applications as a scale remover, for example to remove barium and strontium salts.

The present invention may provide the use of a salt of the first aspect in metal cleaning applications, for example printed circuit boards or electroless plating applications.

The present invention may provide the use of a salt of the first aspect in medical applications, for example, as an anti-poison material. The present invention may be used to assist the delivery of metals to parts of the body.

The present invention may provide the use of a salt of the first aspect in food applications, for example as a stabiliser or antioxidant.

The invention will now be further described by way of the following non-limiting examples.

EXAMPLE 1

Synthesis of Compounds

The components detailed in table 1 were prepared by the following method: In each case, 100.0 g of Enviomet C320 (ethylene diamine disuccinic acid (65% active)) [0.2 moles] was slurried in 1 L de-ionised water and the stated amount of $Mg(OH)_2$ and/or $Ca(OH)_2$ and/or NaOH was added. The mixture was stirred for 17 hours before being filtered. The solution was concentrated and the product was allowed to crystallise out. The white crystalline product was collected by filtration and dried in vacuum oven at 40° C. overnight. The EDDS content was determined by HPLC and the metal content by ICP.

TABLE 1

Preparation and Analysis of Examples

| | Compound(s) added to 0.2 moles of EDDS: | | | | | | Analysis: (g/Kg) | | | | Empirical |
| --- | --- | --- | --- | --- | --- | --- | --- | --- | --- | --- | --- |
| | $Mg(OH)_2$ | | $Ca(OH)_2$ | | NaOH | | | | | | |
| Example | Mass (g) | Moles | Mass (g) | Moles | Mass (g) | Moles | EDDS | Mg | Ca | Na | Formula |
| A | 25.96 | 0.4 | | | | | 676.1 | 111.0 | | | $Mg_{2.0}EDDS$ |
| B | 13.68 | 0.2 | | | | | 694 | 59.3 | | | $Mg_{1.0}EDDS$ |
| C | 20.52 | 0.3 | | | | | 730 | 75.2 | | | $Mg_{1.2}EDDS$ |
| D (Comparative) | 6.84 | 0.1 | | | 13.31 | 0.3 | 750 | 31.3 | | 81.2 | $Mg_{0.5}Na_{1.4}EDDS$ |
| E | 13.67 | 0.2 | 16.29 | 0.2 | | | 654.6 | 45.8 | 70.2 | | $Ca_{0.8}Mg_{0.8}EDDS$ |
| F (Comparative) | | | 32.58 | 0.4 | | | 723.1 | | 199.0 | | $Ca_2EDDS$ |
| G | 12.98 | 0.2 | | | 17.81 | 0.4 | 656.7 | 109.7 | | 50.8 | $Na_{2.1}Mg_{0.9}EDDS$ |

EXAMPLE 2

The appearance of each of the materials was observed periodically over 72 hours. The observations are recorded in table 2.

TABLE 2

| Example | Initial Appearance | Appearance after 24 hr | Appearance after 48 hr | Appearance after 72 hr |
| --- | --- | --- | --- | --- |
| $Na_3EDDS$ | Free flowing powder | Sticky Solid (2 hr) | Very Sticky Solid | Very Sticky Solid |
| A | Free flowing powder | Free flowing powder | Free flowing powder | Free flowing powder |
| B | Free flowing powder | Free flowing powder | Free flowing powder | Free flowing powder |
| C | Free flowing powder | Free flowing powder | Free flowing powder | Free flowing powder |
| D (Comparative) | Free flowing powder | Slightly Sticky powder | Slightly Sticky powder | Slightly Sticky powder |
| E | Free flowing powder | Free flowing powder | Free flowing powder | Free flowing powder |
| F (Comparative) | Free flowing powder | Slightly Sticky powder | Slightly Sticky powder | Slightly Sticky powder |
| G | Free flowing powder | Free flowing powder | Free flowing powder | Free flowing powder |

Table 3 show how the samples increased in mass over time.

TABLE 3

| Example | % increase in mass after 72 hr |
|---|---|
| A | 0.10% |
| B | 0.84% |
| C | 0.46% |
| D (Comparative) | 5.48% |
| E | 0.32% |
| F (Comparative) | 8.81% |
| G | 1.26% |
| Na$_3$EDDS | 25% |

EXAMPLE 3

Solubility

The solubility of each sample was measured as follows: An excess of solid material was added to 5 ml of water and stirred overnight at room temperature. The solution was filtered and the filtrate analysed for EDDS content by HPLC. The solubility values given in table 4 refer to the amount of free EDDS or succinate ion present and ignore the mass of any associated counter ion.

TABLE 4

| Example | EDDS content of a saturated solution solubility (g/kg) |
|---|---|
| EDDS•nH$_2$O | 0.3 |
| A | 164.3 |
| B | 17.3 |
| C | 93.6 |
| D (Comparative) | 61.9 |
| E | 65.3 |
| F (Comparative) | 10.1 |
| G | >300 |

The invention claimed is:

1. A method of preparing a composition comprising a salt of ethylenediamine disuccinic acid comprising at least 0.7 mole equivalents of magnesium per mole of ethylenediamine disuccinic acid and one or more further components, the method comprising admixing the salt in the form of a water-soluble, non-hygroscopic solid with said one or more further components.

2. The method according to claim 1, wherein the salt comprises at least 0.9 moles magnesium per mole of ethylenediamine disuccinic acid.

3. The method according to claim 1, wherein the salt comprises at least 1.8 moles of magnesium per mole of ethylenediamine disuccinic acid.

4. The method according to claim 1, wherein the salt absorbs less than 5% of its weight of water upon exposure to standard atmospheric conditions for 72 hours.

5. The method according to claim 1, wherein the salt has a solubility which provides a concentration of EDDS of at least 10 g/Kg.

6. The method according to claim 1, wherein the salt is in the form of free flowing particulate material.

7. The method according to claim 1, wherein the composition is a granular composition.

8. The method according to claim 1, comprising adding a base of an alkaline earth metal to ethylenediamine disuccinic acid.

9. The method according to claim 1 wherein said composition comprises hydrogen peroxide or other peroxygen-containing compound or precursor thereof and wherein the stability of said composition is improved.

10. The method according to claim 1, wherein said composition is a chelating agent, an anti-sealant material or a scale remover.

11. The method according to claim 1, wherein said composition is a detergent composition.

12. The method according to claim 1, wherein said composition is a personal care or cleaning composition or is a biocide potentiator.

13. The method according to claim 1, wherein said composition is an agricultural, food or medical composition.

14. The method according to claim 1, wherein said composition is a pulp or paper bleaching composition.

* * * * *